(12) United States Patent
Mernoe et al.

(10) Patent No.: US 8,653,976 B2
(45) Date of Patent: Feb. 18, 2014

(54) COMBINATION OF A PORTABLE MONITORING DEVICE AND A PORTABLE DRIP INFUSION SET AND A METHOD OF MONITORING A PORTABLE DRIP INFUSION SET

(75) Inventors: Morten Mernoe, Charlottenlund (DK); Morten Thing, Espegaerde (DK)

(73) Assignee: Dripmate A/S, Charlottenlund (DK)

( * ) Notice: Subject to any disclaimer, the term of this patent is extended or adjusted under 35 U.S.C. 154(b) by 440 days.

(21) Appl. No.: 13/041,977

(22) Filed: Mar. 7, 2011

(65) Prior Publication Data

US 2011/0221596 A1 Sep. 15, 2011

Related U.S. Application Data

(60) Provisional application No. 61/312,334, filed on Mar. 10, 2010.

(51) Int. Cl.
*G08B 23/00* (2006.01)
*G08B 13/14* (2006.01)

(52) U.S. Cl.
USPC ............... 340/573.1; 340/568.1; 340/539.12; 604/251

(58) Field of Classification Search
USPC ........... 340/573.1, 568.1, 571, 539.1, 539.11, 340/539.12, 539.13, 539.15, 539.19, 340/539.21, 539.23, 539.32, 540, 573.4; 604/251

See application file for complete search history.

(56) References Cited

U.S. PATENT DOCUMENTS

| | | | | |
|---|---|---|---|---|
| 7,782,192 B2 * | 8/2010 | Jeckelmann et al. | .... | 340/539.12 |
| 8,487,758 B2 * | 7/2013 | Istoc | ........ | 340/539.15 |
| 2003/0043037 A1 * | 3/2003 | Lay | ............. | 340/568.1 |
| 2006/0001550 A1 * | 1/2006 | Mann et al. | ............. | 340/870.07 |
| 2011/0071464 A1 * | 3/2011 | Palerm | ............ | 604/66 |

FOREIGN PATENT DOCUMENTS

| | | |
|---|---|---|
| DE | 10 2005 031 754 A1 | 1/2007 |
| WO | WO 2007/020650 A2 | 2/2007 |
| WO | WO 2009/109559 A1 | 9/2009 |

* cited by examiner

*Primary Examiner* — Anh V La
(74) *Attorney, Agent, or Firm* — Merchant & Gould P.C.

(57) ABSTRACT

There is provided a combination of a portable monitoring device for monitoring a portable drip infusion set for use in hospitals and the like and the portable drip infusion set, preferably being of the type comprising a liquid supply, a drip chamber downstream of the liquid supply for forming liquid drops and a flexible tube connecting the drip chamber with an injection needle.

26 Claims, 9 Drawing Sheets

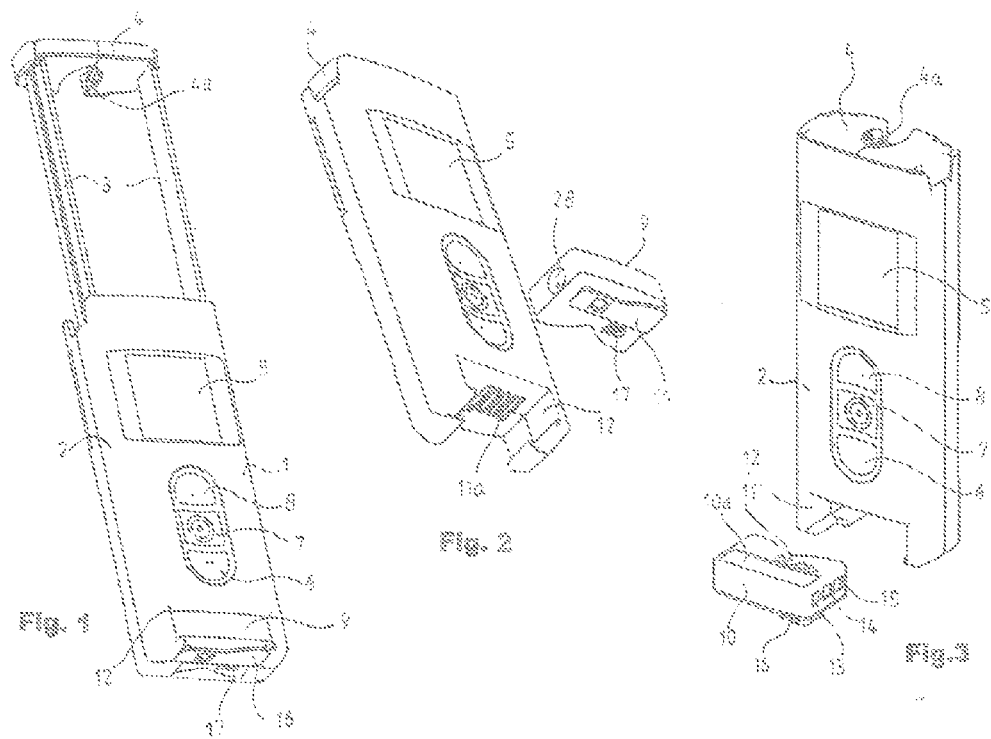

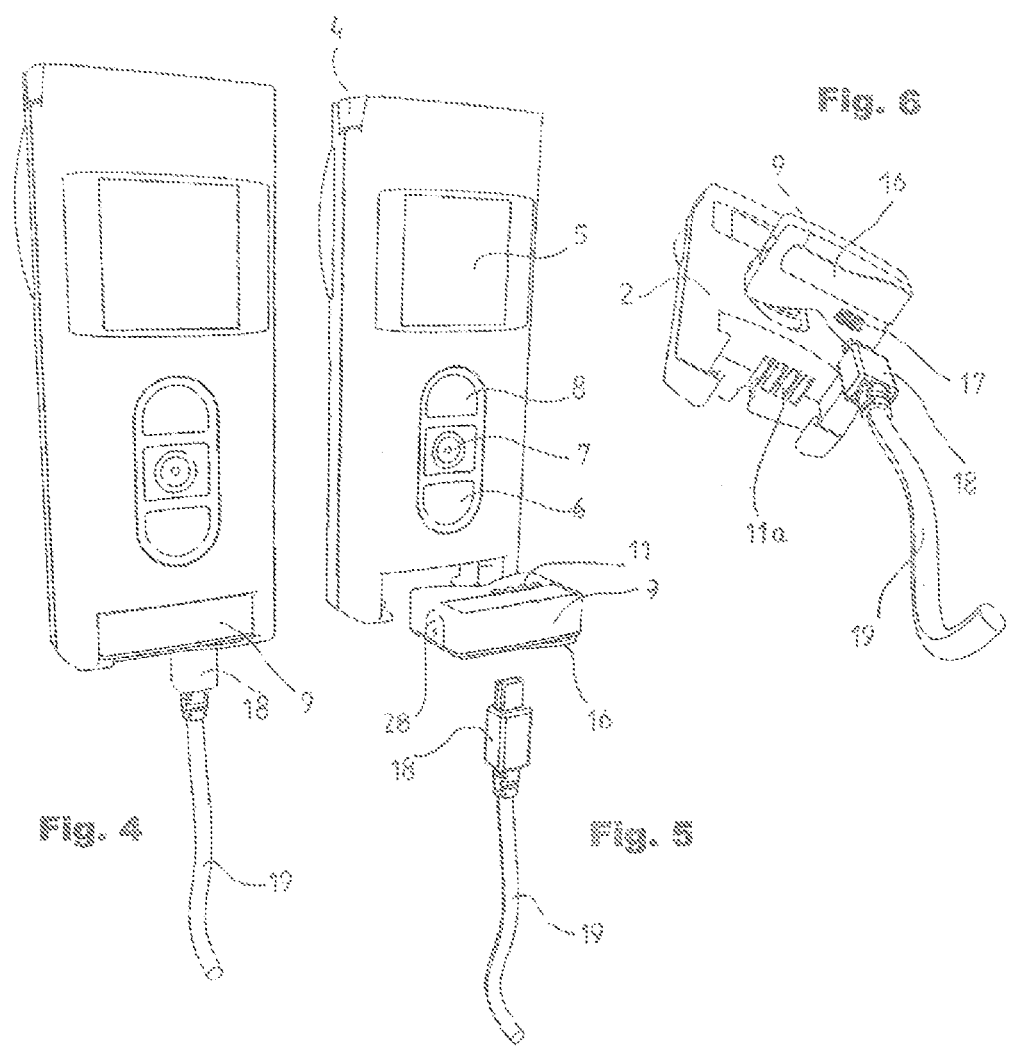

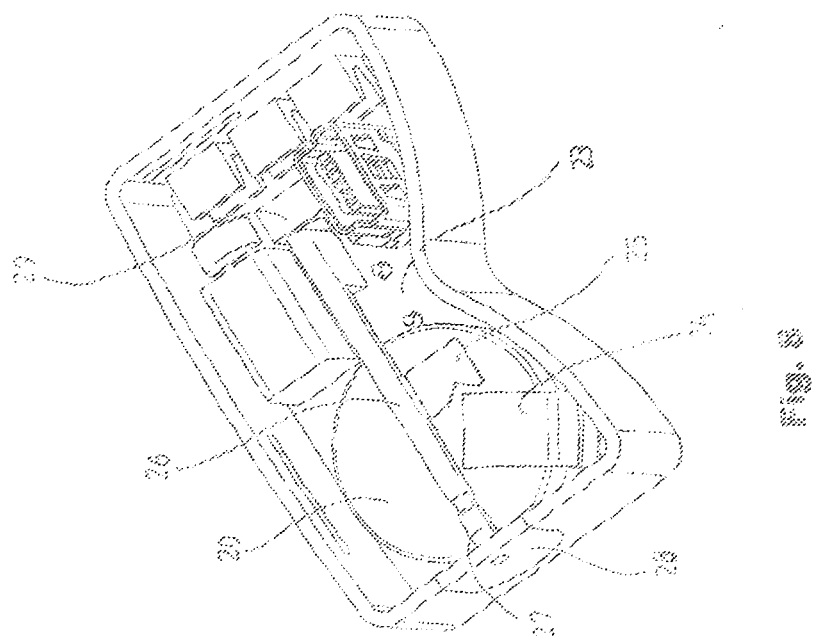
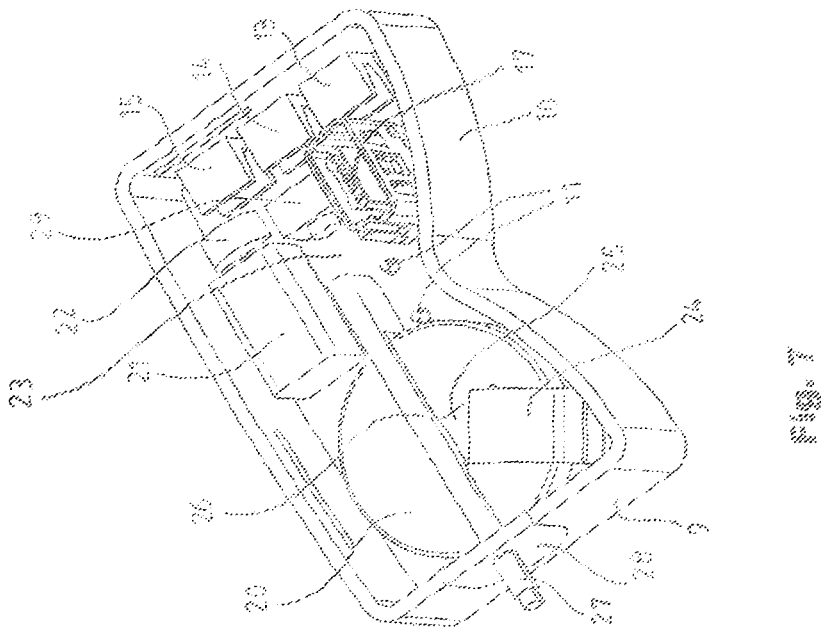

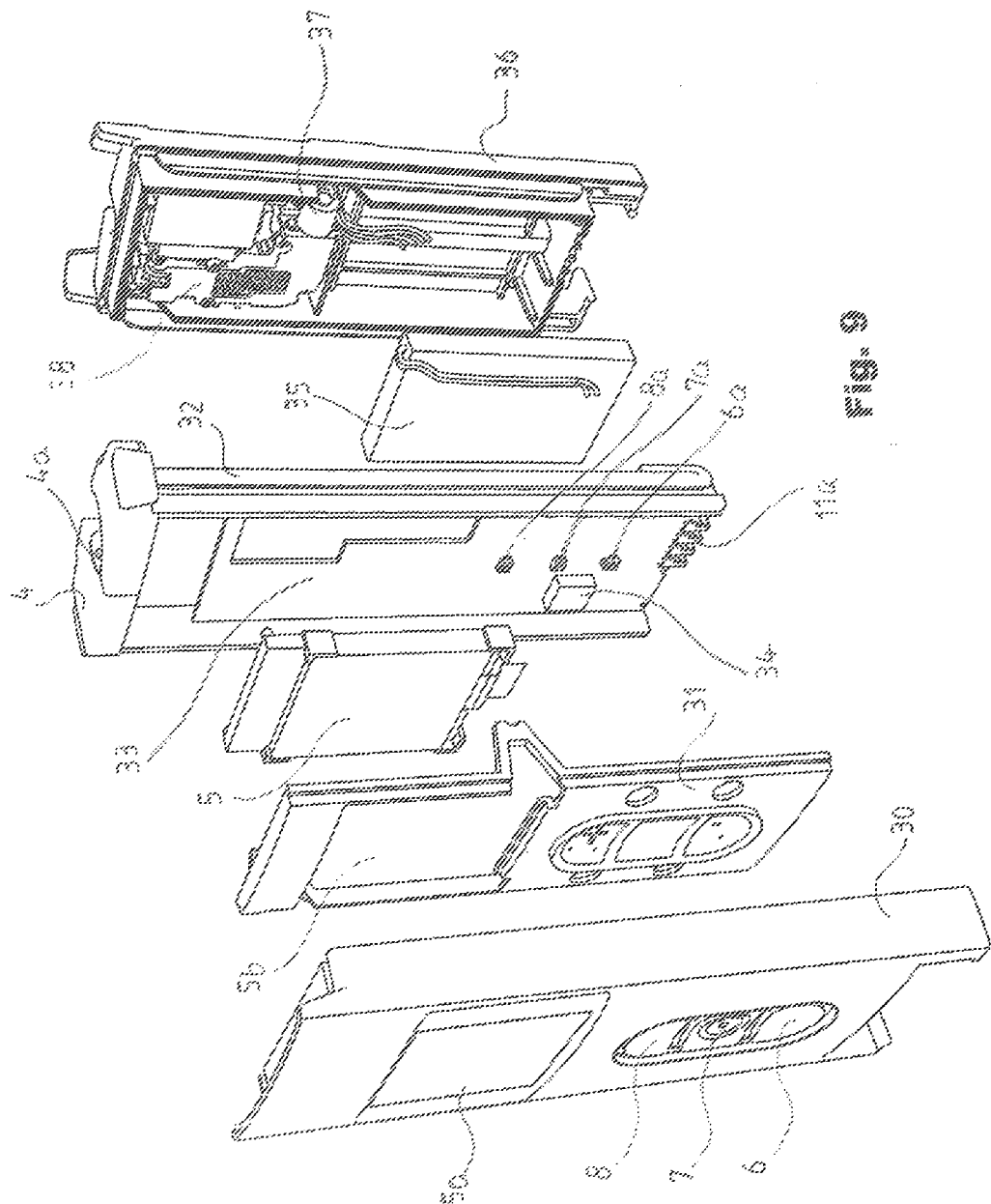

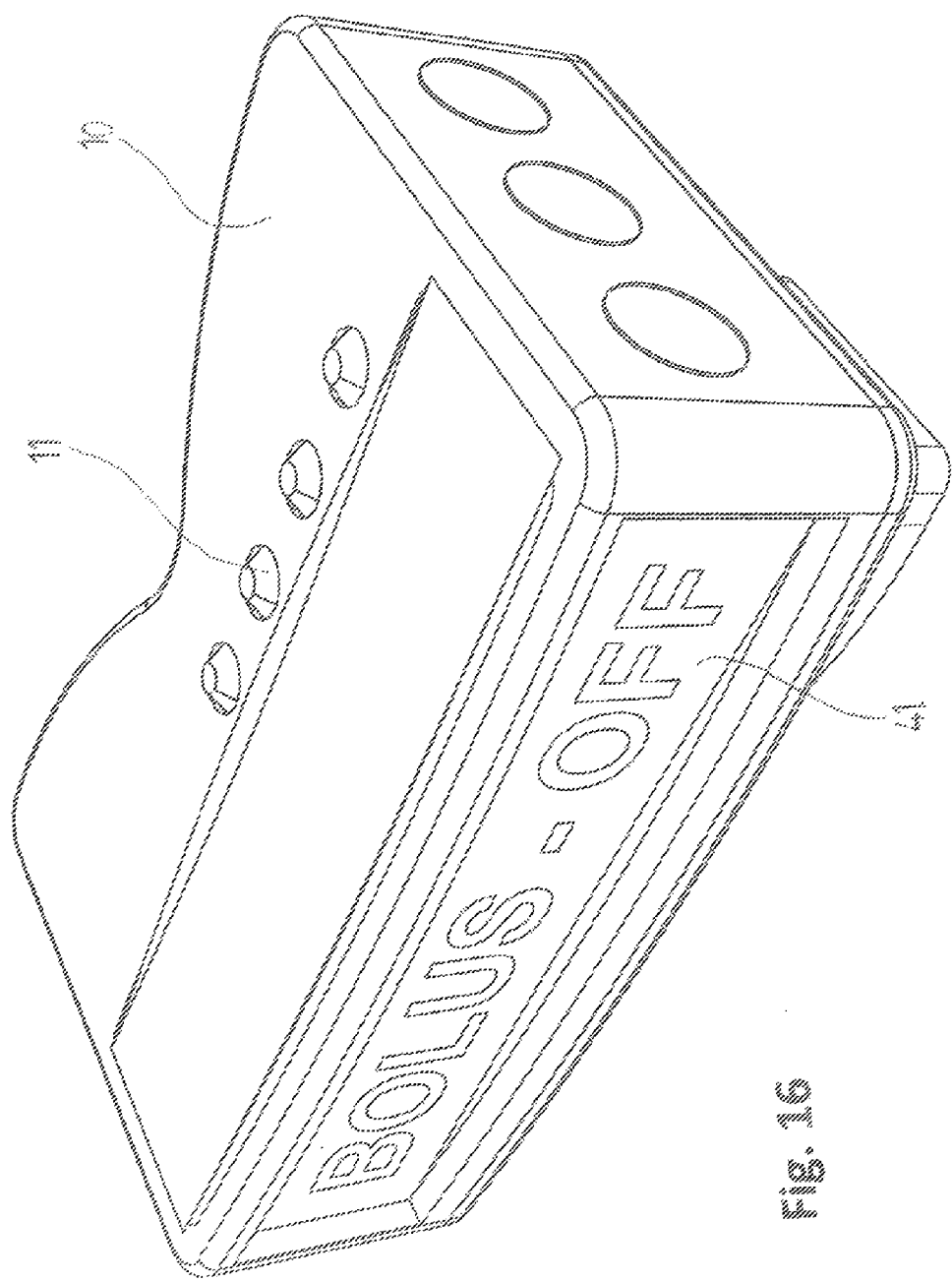

COMBINATION OF A PORTABLE MONITORING DEVICE AND A PORTABLE DRIP INFUSION SET AND A METHOD OF MONITORING A PORTABLE DRIP INFUSION SET

RELATED APPLICATION

This application claims benefit of Ser. No. 61/612,334, filed 10 Mar. 2010 in the United States and which application is incorporated herein by reference. A claim of priority to the extent appropriate is made.

FIELD OF THE INVENTION

The present invention relates to a combination of a portable monitoring device for monitoring a medical device in the form of a portable drip infusion set for use in hospitals and the like and of the type comprising a liquid supply, a drip chamber downstream of said liquid supply for forming liquid drops and a flexible tube connecting said drip chamber with an injection needle.

BACKGROUND

In connection with portable medical devices of this type it is a problem that the devices are stolen which is financially harmful and can be life-threatening if the stolen device is required in an emergency.

It is therefore an object of the invention to provide a system for registering that a medical device has been removed from a certain area with a very small time lag from removal to registration of removal.

SUMMARY

According to the invention, this object is achieved by said monitoring device comprising:
  a first housing, a signal receiver for receiving a first wireless signal, a first timing device for measuring a time interval, preferably 30 seconds, an alarm device for emitting a first alarm, first electronic circuitry interconnecting said signal receiver, said first timing device and said alarm device for causing said alarm device to emit said first alarm if said first signal is not received by said signal receiver at the end of said time interval, and a first battery for providing electric energy to said signal receiver, said alarm device and said first timing device, and
said medical device comprising:
  a second housing, a signal emitter for emitting said first wireless signal, a second timing device for measuring said time interval, second electronic circuitry interconnecting said timing device and said signal emitter for causing said signal emitter to emit said first signal at the end of said time interval, and an electric power supply, preferably a second battery, for providing electric energy to said timing device and said signal emitter.

Hereby, if and when the medical device is displaced so far away from the intended place of use thereof that the medical device is out of the receiving range of the signal receiver of the monitoring device, then the monitoring device will emit an alarm at the end of the time interval after it has received said first signal (a so-called hand shake signal) for the last time. If this time interval is short, for instance 30 seconds, then it is possible to react quickly and have a better chance than otherwise to stop the theft. In some cases, the theft takes place while the medical device is in use, and thereby the patient supposed to be treated by the medical device may be harmed or placed in jeopardy so that even if the theft is not prevented, at least it is registered that the medical device in question is not being used in the intended manner and relevant steps can be taken to protect the patient in question.

In the currently preferred embodiment of the invention said alarm device is adapted for emitting a second alarm and said signal emitter is adapted for emitting a second wireless signal, said monitoring device comprising third electronic circuitry adapted for registering receipt of said second signal by said signal receiver and causing said alarm device to emit said second alarm if said second signal is received by said signal receiver, and said medical device comprising fourth electronic circuitry being adapted for monitoring functional parameters of said medical device such as voltage of said power supply or second battery, any pre-determined output from said medical device or the function of said fourth electronic circuitry and further being adapted for registering deviations from pre-determined values of said functional parameters and causing said signal emitter to emit said second signal if said deviations are registered.

Thus, any malfunction of the medical device that is considered serious enough to warrant an alarm will be brought to the attention of the health care person or persons monitoring the monitoring device such that an appropriate reaction can take place to safeguard the patient in question.

Preferably, said monitoring device and said medical device comprise first and second sets of electrical contacts, respectively, for mutually electrically interconnecting said monitoring device and said medical device for transmitting electronic data and/or electrical power between said monitoring device and said medical device.

Hereby the monitoring device may be used for transferring electronic data to the medical device or receive and store electronic data from the medical device as well as for receiving or transmitting electric power from or to the medical device.

In the currently preferred embodiment of the invention said medical device comprises programming means such as a push button, a switch, a keyboard, a data transmission receiver, a data input port or the like for programming fifth electronic circuitry controlling the function of said medical device, said fifth electronic circuitry comprising blocking means for blocking said programming function of said programming means when said monitoring device is not electrically connected to said medical device through said first and second electrical contacts.

This is a valuable security measure that prevents unauthorized programming or amendment of programming of the medical device operations without access to the monitoring device which ideally is in the hands of an authorized health care worker.

In the currently preferred embodiment of the invention said monitoring device housing comprises an input port for receiving a data/electrical power plug such as a USB plug, said input port being electrically connected to said first set of electrical contacts such that data and electrical power can be transmitted to said medical device from said input port when said first and second sets of electrical contacts are interconnected.

Preferably, said monitoring device and said medical device comprise first and second sets of attachment means, respectively, for detachably attaching said monitoring device to said medical device such that said first and second sets of electrical contacts are interconnected.

In the currently preferred embodiment of the invention, said first and second alarms comprise one or more of a sensory alarm such as a vibrator, a visual alarm such as lamps of different colours and an audible alarm.

In the currently preferred embodiment of the invention, said monitoring device housing comprises attachment means such as a clip for attaching said monitoring device to the apparel of a health care provider.

Advantageously, said monitoring device housing comprises means such as push buttons or switches for manually interrupting said first and second alarms.

In the currently preferred embodiment of the invention, said first and second signals comprise a code recognizable by said first and third electronic circuitry of said monitoring device.

Hereby, a certain medical device will be "paired" with a certain monitoring device which will allow several "pairs" of medical and monitoring devices to be operational on the same premises without interfering with one another.

In the currently preferred embodiment of the invention, said code is generated by fifth electronic circuitry of said medical device and transmitted to said first and third electronic circuitry of said monitoring device through said first and second sets of electric contacts.

In the currently preferred embodiment of the invention, said electronic circuitry of the medical device comprises blocking means for blocking transmittal of data and electrical power to said medical device if said first and second electrical contacts are not in mutual electrical contact.

Hereby, it is achieved that no unauthorized programming or amendment of the authorized programming may take place unless the responsible health care take connects the monitoring device to the medical device. Furthermore, the value of the medical device, if stolen, will be diminished as it cannot be used without a corresponding monitoring device.

The medical device and said monitoring device each comprise a microprocessor arranged in a printed circuit board (PCB), said microprocessors being in electrical contact for exchanging electronic data and said medical device microprocessor controlling the operation of said medical device.

In an advantageous embodiment of the combination according to the invention the monitoring device microprocessor is pre-programmed to transmit solely one specific set of operating instructions to said medical device microprocessor.

In an advantageous embodiment of the combination according to the invention, said housing of said monitoring device is provided with a display adapted for displaying information in a visual manner.

Preferably, said display is adapted to display information generated by said monitoring device microprocessor.

Advantageously, said signal emitter may be adapted for emitting a third wireless signal comprising operational data of said medical device generated by said medical device microprocessor, and said display means may be adapted for displaying information based on said operational data transmitted by said third wireless signal and received by said signal receiver of said monitoring device.

Hereby, the responsible health care person can continuously remotely monitor the operation of the medical device.

In some cases it may be an advantage that said medical device is adapted to omit any one of said first, second and third signals. Hereby the monitoring device may be utilized solely to transmit operational data or a malfunction alarm or a hand shake or any combination of two of these functions.

In a further aspect, the invention relates to a monitoring device as set out above.

In a yet further aspect, the invention relates to a medical device as set out above.

In a final aspect, the invention relates to a method of monitoring the function of a medical device for use in hospitals and the like and in the form of a portable drip infusion set of the type comprising a liquid supply, a drip chamber downstream of said liquid supply for forming liquid drops and a flexible tube connecting said drip chamber with an injection needle, the method comprising the steps of:

providing a portable monitoring device able to receive wireless signals from said medical device, causing said medical device to send a first wireless signal at certain time intervals, preferably every 30 seconds, and causing said monitoring device to emit a first alarm if said monitoring device does not receive said first signal after said time interval has elapsed.

In the currently preferred embodiment of the invention, the method comprises the further steps of:

causing said medical device to send a second wireless signal if said medical device develops a malfunction, causing said monitoring device to emit a second alarm if said monitoring device receives said second signal.

In the currently preferred embodiment of the invention, said medical device and said monitoring device each are provided with collaborating electrical contacts for establishing direct electrical contact between said monitoring device and said medical device for transmitting electrical energy and electronic data, and the functions of said medical device are programmable only when said direct electrical contact is uninterrupted.

In the currently preferred embodiment of the invention, the method comprises the steps of:

electrically connecting said monitoring device to said medical device, programming the functions of said medical device, removing said monitoring device from electrical contact with said medical device, and monitoring said monitoring device so as to register whether an alarm is emitted by said monitoring device.

In the currently preferred embodiment of the invention, the method comprises the steps of:

causing said medical device to generate a code, transmitting said code to said monitoring device, incorporating said code in said first and second wireless signals.

Advantageously, said medical device comprises a first microprocessor for controlling the function of said medical device and said monitoring device comprises a second microprocessor adapted to communicate with said first microprocessor when said monitoring device is in electrical connection with said medical device and the method according to the invention comprises the steps of:

programming said second microprocessor, electrically connecting said monitoring device with said medical device, and transmitting data from said second microprocessor to said first microprocessor.

In a further embodiment, the method according to the invention may comprise the steps of:

generating operating data regarding the functioning of said medical device in said first microprocessor, transmitting said operating data to said monitoring device, storing said operating data in said monitoring device, and transmitting said operating data from said monitoring device to an electronic entity such as a PC.

Hereby the treatment of the patient may be recorded and entered into the patient's medical records.

Advantageously, said monitoring device is provided with a display, the method comprising the further step of displaying information relative to the specific programming of said monitoring device.

Advantageously, said method may comprise the further steps of causing said medical device to transmit said operating data to said monitoring device by means of a third wireless signal and displaying said operating data by means of said display.

In some cases it may be advantageous that any one of said first, second and third wireless signals is omitted. Hereby the monitoring method may be utilized solely to transmit operational data or a malfunction alarm or a hand-shake or any combination of two of these functions.

BRIEF DESCRIPTION OF THE DRAWINGS

In the following, the invention will be explained more in detail in connection with the currently preferred embodiment thereof shown, solely be way of example, in the accompanying drawings, where:

FIG. 1 is a schematic, perspective view of a combination according to the invention with the monitoring device attached to a medical device in the form of a portable drip infusion device which is monitored by the monitoring device, FIG. 2 is a schematic perspective view corresponding to FIG. 1 with the monitoring device shown separated from the medical device, FIG. 3 is a schematic perspective view corresponding to FIG. 2 but seen from another angle, FIGS. 4-6 are schematic perspective views corresponding to FIGS. 1-3 illustrating the supply of electrical power and/or data to the monitoring device and the medical device, FIGS. 7-8 are schematic enlarged perspective views of the monitoring device with the bottom covering wall removed to show the interior structure, FIG. 9 is a schematic perspective exploded view of the medical device monitored by the monitoring device, FIG. 16 is a larger scale schematic perspective view of a yet further embodiment of a monitoring device according to the invention, seen from the top.

DETAILED DESCRIPTION

Figure 10:
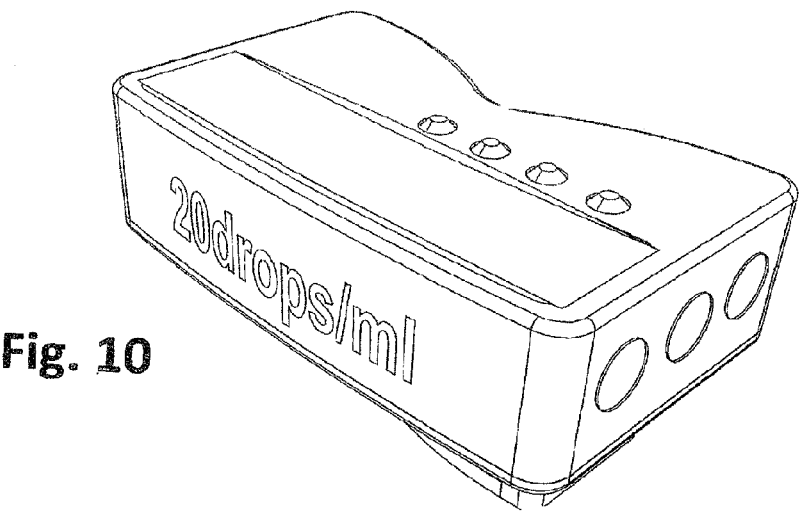
FIGS. 10-12 are schematic, perspective views of three alternative embodiments of a monitoring device according to the invention.

Referring now to FIGS. 1-3, a medical device 1 in the form of a portable drip infusion device has a housing 2 and two telescopically displaceable arms 3 carrying a gripping mechanism 4 for gripping a not shown drip chamber and sensors 4a for sensing drops falling through said drip chamber. The device 1 has a display 5 for displaying information regarding the function of the device. Push buttons 6, 7 and 8 are provided for manually programming the function of the device, button 6 being for decreasing flow of infusion liquid, button 7 being for activating the device and button 8 being for increasing the flow of infusion liquid.

A monitoring device 9 according to the invention has a housing 10 and four electrical contact pins 11 for electrically contacting four corresponding electrical contact plates 11a arranged in a recess 12 in the bottom of housing 2, the recess being adapted for receiving the monitoring device 9.

The monitoring device 9 is provided with three LED light emitters 13, 14 and 15 adapted for emitting white, red and green light, respectively. The monitoring device is further provided with a clip 16 for attaching the monitoring device to the front of a pocket or the like of a health care worker responsible for monitoring the medical device. A space 10a on the housing 10 is provided for marking the monitoring device 9 with an erasable marker for instance to visually identify the medical device which is being monitored by the monitoring device.

Referring now to FIGS. 4-6, the monitoring device 9 is further provided with a socket for receiving a miniature USB plug 18 for supplying electrical power and/or data transmission from a cable 19 to the monitoring device 9/medical device 1 as explained more in detail in the following.

Referring now to FIGS. 7 and 8 illustrating the monitoring device seen from the bottom (with the bottom wall removed) and in storage mode and in active mode, respectively, the housing 10 contains a rechargeable battery 20, a vibrator motor 21 and a vibrator 22, three LED light emitters 13-15 (green, yellow and red, respectively), a printed circuit board (PCB) 23, a battery contact plate 24 and an insulating plate 25 attached to a push rod 26. A mini USB socket 17 is electrically connected to the PCB 23. The PCB 23 comprises a not shown microprocessor.

Two electrical contacts 11 are connected to the PCB 23, the other two electrical contacts are hidden behind the socket 17 and the battery 20 and are also connected to the PCB 23. Two of the contacts 11 serve for transmitting electrical power and two contacts 11 serve for data transmission.

The push rod 26 has a telescopically displaceable portion 27 and is mounted on a displaceable plate 28. A switch 29 serves to stop the vibrator motor 21 when the plate 28 and rod 26 are displaced to the right from the position shown in FIG. 8 by finger pressure exerted by the responsible health care provider as explained more in detail in the following.

Referring now to FIG. 9 illustrating the portable drip infusion device 1 with some of the different components thereof exposed in an exploded view, a front cabinet 30 is provided with the push buttons 6-8 and is assembled with a moisture insulating rubber seal 31 unto the main body 32 of the device 1 with the display 5 received in apertures 5a and 5b in front cabinet 30 and insulating seal 31.

The main body 32 contains a printed circuit board (PCB) 33 comprising a not shown microprocessor for controlling the functions of medical device 1, generating a code for the wireless signals, programming of the functions of the medical device 1, monitoring said functions to register any malfunction of the device 1 and generating said second signal in case of a malfunction, measuring time for determining the emission of said first signal and generating said first signal and generating operational data for being displayed in the display 5.

An audible alarm 34 is mounted on the PCB 33 and switches 6a, 7a and 8a are mounted on the PCB to be activated by the push buttons 6, 7 and 8, respectively.

Four electrical contacts 11a for contacting the corresponding contacts 11 of the monitoring device 9 are also connected to the PCB 33.

A rechargeable battery 35 is mounted between the main body 32 and a rear cabinet 36 containing elements for the function of the medical device 1 such as a motor 37 and a gear box 38 for regulating the flow of infusion liquid.

In use, the monitoring device shown in FIG. 7 is readied for its first time use by pressing the portion 27 of the rod 26 such that the rod is displaced to the right in FIG. 7 whereby the insulating plate is displaced to the position shown in FIG. 8 where it does not prevent contact between the battery 20 and the battery contact plate whereby power is now supplied to the PCB 23. Hereby, it is avoided that the battery 20 is discharged during storage prior to first use of the monitoring device 9.

The monitoring device 9 is inserted in the recess 12 in the medical device 1 such that the contacts 11 and 11a are electrically connected. The mini USB plug 18 may, if necessary, be inserted in the socket 17 to recharge the batteries 20 and 35 and perhaps transmit electronic data to the microprocessor of the medical device 1. The battery 35 of the medical device can only be recharged through the corresponding monitoring device's USB plug 18.

The rate of flow of the infusion device 1 is set by means of the buttons 6 and 8. A code is generated by the microprocessor incorporated in the PCB 33 of the medical device 1 and transmitted to and stored in the microprocessor incorporated in the PCB 23 of the monitoring device 9 through the contacts 11 and 11a. This allows several different medical devices to be "paired" with each its own monitoring device in the same hospital.

The medical device 1 is activated by pressing the button 7 and the monitoring device is removed from the recess 12 and for instance clipped to the breast pocket of the responsible health care provider.

The green LED 13 blinks as long as the medical device 1 is functioning correctly and the battery 35 thereof has sufficient power.

Every 30 seconds the signal emitter incorporated in the PCB 33 of the medical device 1 sends a "hand shake" signal with the code incorporated, and as long as the medical device is within receiving range of the signal receiver incorporated in the PCB 23 of the monitoring device and therefore the signal is received by the signal receiver, the monitoring device will not react. However, if the hand shake signal is not received after the elapse of 30 seconds after the last hand shake signal was received, the vibrator 22 of the monitoring device will be activated and the yellow LED 14 will start blinking which will indicate that the medical device has been moved out of range of the monitor device's signal receiver.

The health care provider can stop the vibrator by pushing on the push button 28 thereby activating the vibrator interruption switch 22, but the yellow LED 14 will continue blinking until a new hand shake signal is received.

The microprocessor incorporated in the PCB 33 of the medical device monitors the correct operation of the medical device and the condition of the battery 35. If a malfunction is detected, an alarm signal will be transmitted by the signal transmitter incorporated in the PCB 33. When this alarm signal is received by the signal receiver incorporated in the PCB 23, the vibrator 22 will be activated, and the red LED 15 will start blinking. The vibrator can be deactivated by pushing the button 28, but the red LED 15 will continue blinking until the monitoring device is inserted into the recess 12 of the medical device.

As a further embodiment of the combination according to the invention as an alternative to the medical device 1, for instance a drip infusion set, being programmed with specific functional parameters, in the case of drip infusion sets, drop size and flow rate by the user (nurse) when setting up the treatment of a patient this programming step by the nurse can be eliminated.

In some hospital or clinic environments it is preferred only to use one specific drop set or drip chamber and therefore only utilize one specific drop size. Then there is no need for the user to programme drop size into the medical device, and eliminating programming of drop size also eliminates the risk of programming the wrong drop size into the device.

In that case it would be an advantage to the user if the monitoring device used is able to programme the device with a specific drop size even though the medical device is adapted to be programmed for several different drop sizes.

To achieve this advantage the microprocessor of the PCB 23 of the monitoring device is factory programmed to a specific drop size and marked (see FIG. 10) or colour coded to indicate to the user whether the monitoring device will programme the medical device to: 10, 15, 20, 30, 40, 50 or 60 drop/ml (or any other suitable number).

Of course, this alternative also applies to other programmable medical devices for use in a combination according to the invention.

In some environments only one type of infusion is performed and therefore only one flow rate needs to be programmed, and in these cases it would be an advantage to the user if the monitoring device used is able to programme the medical device with a specific flow rate even though the medical device is adapted to be programmed for several different flow rates.

Figure 11:
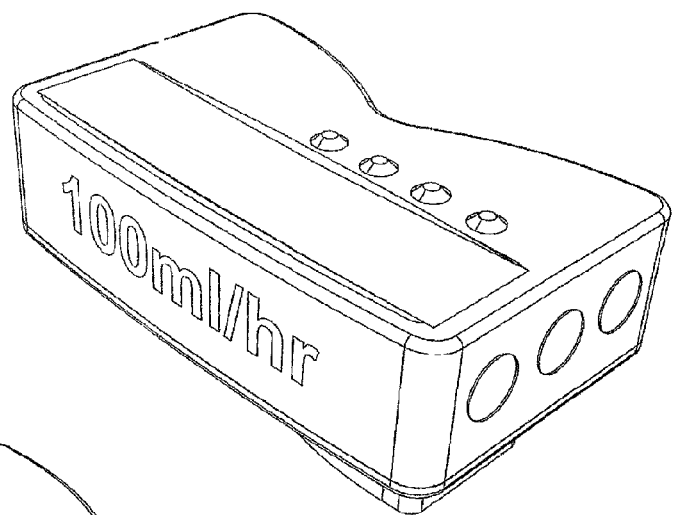

To achieve this advantage the monitoring device microprocessor is factory programmed to a specific flow rate and marked (see FIG. 11) or colour coded to indicate to the user whether the monitoring device will programme the medical device to: 10, 50, 100, 150, 200 or 250 ml/hr (or any other suitable number).

Figure 12:
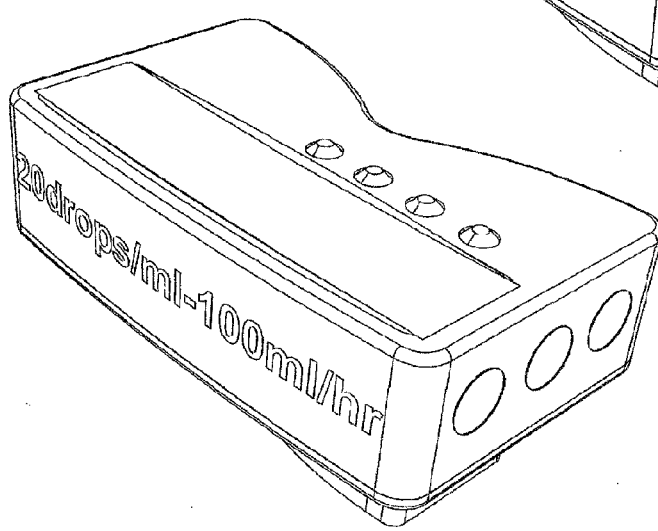

Alternatively, the monitoring device microprocessor can be factory programmed with both a specific drop size and a specific flow rate in cases where the user always uses the same specific drop set and only at a specific flow rate (see FIG. 12).

Figure 13:
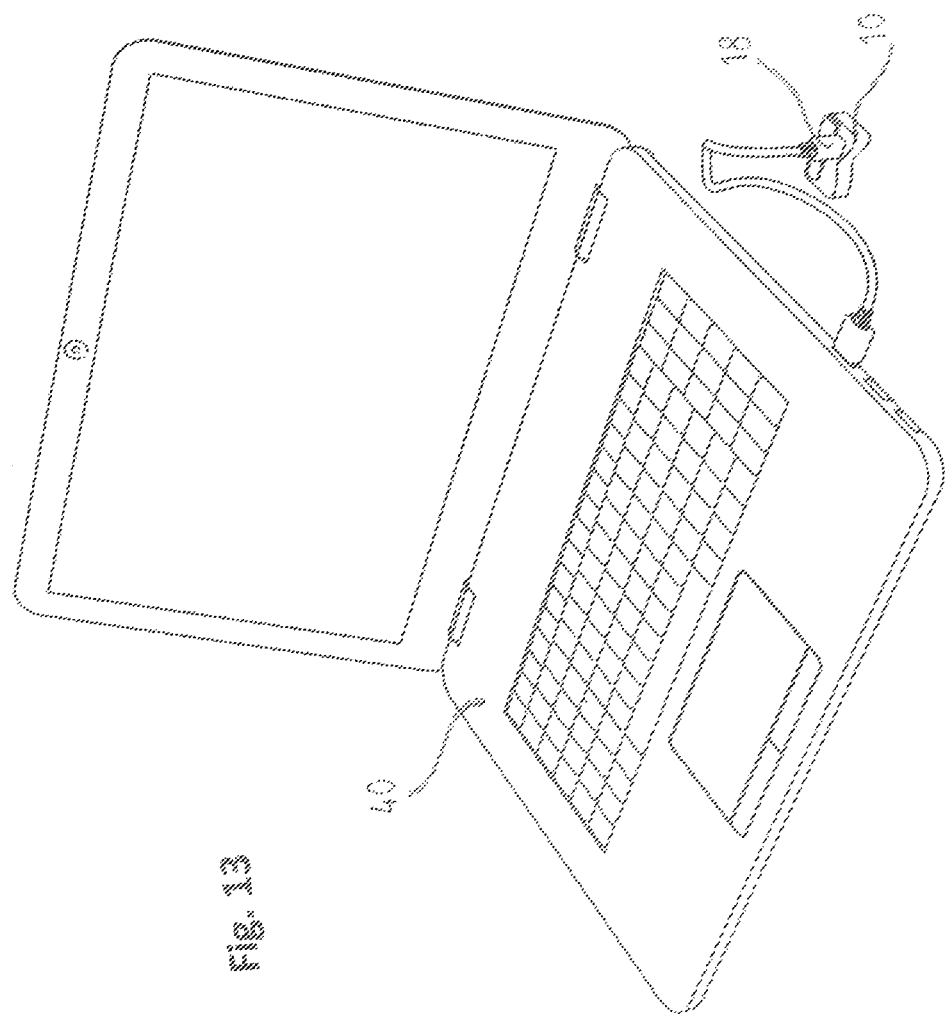
FIG. 13 is a larger scale schematic perspective view of the interconnection of a monitoring device according to the invention and a personal computer (PC)
Figure 14:
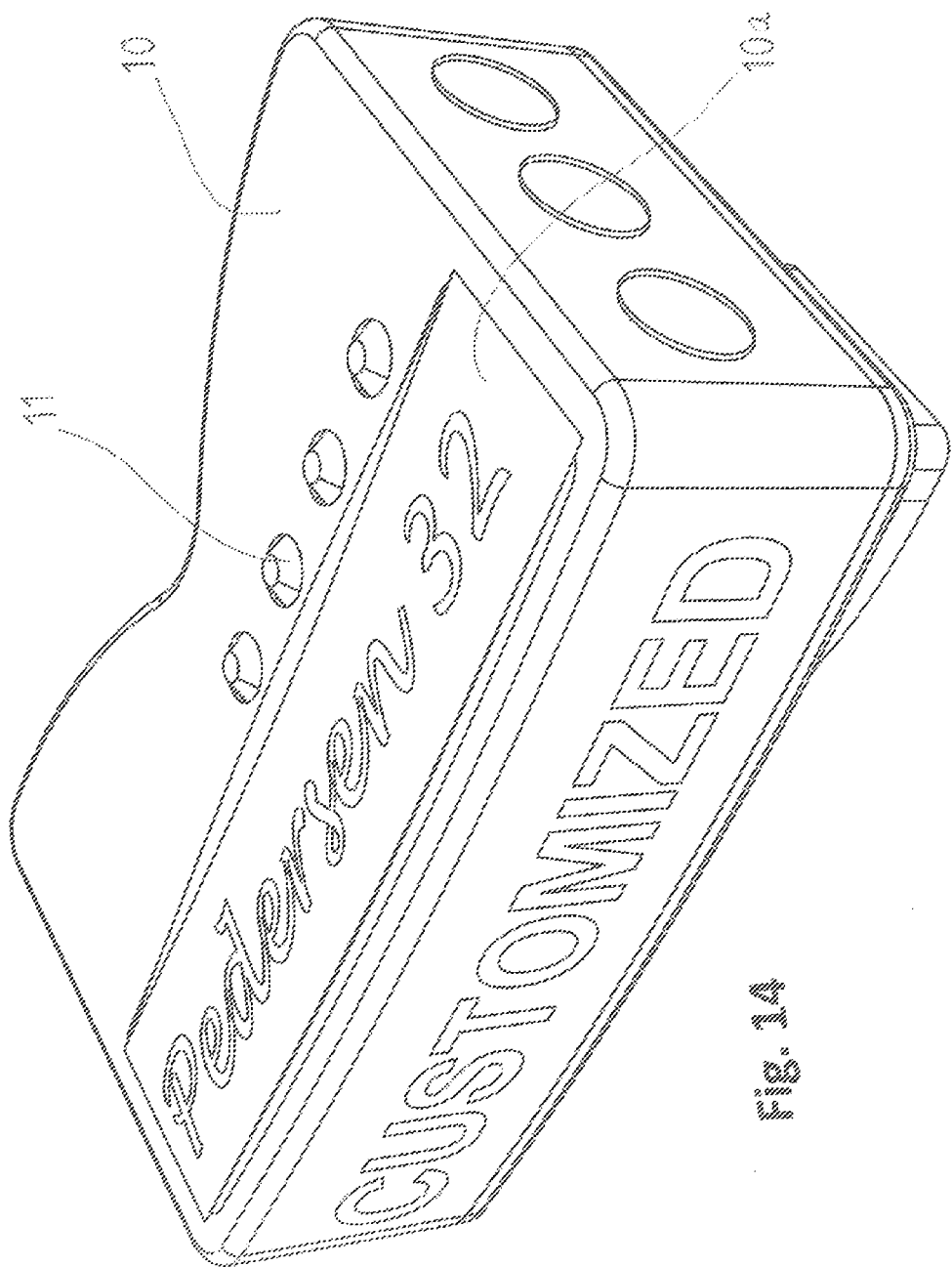
FIGS. 14-15 are schematic enlarges scale perspective views of a further embodiment of monitoring device according to the invention, seen from the top and the bottom, respectively.
Figure 15:
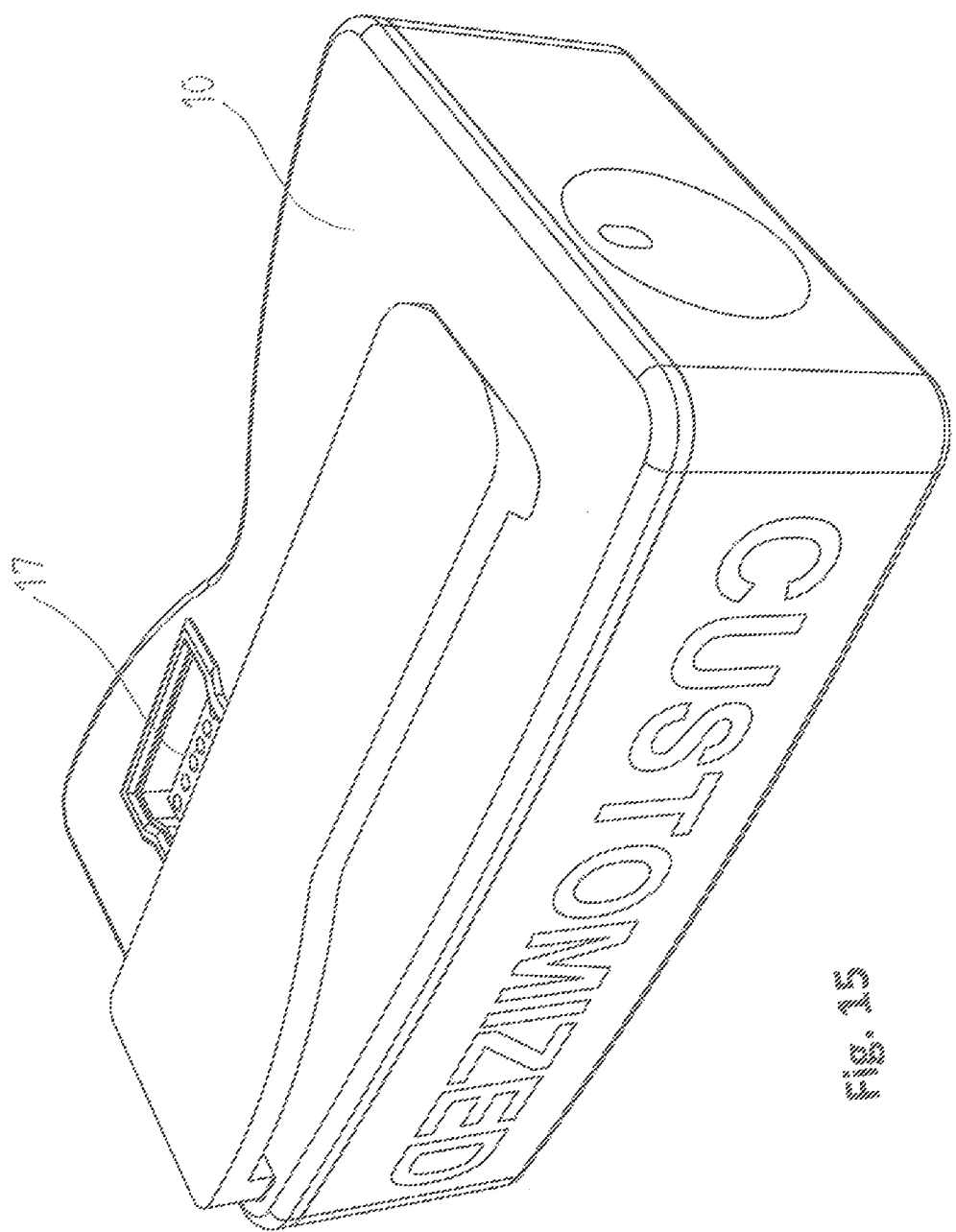

Reference is now made to FIG. 13-15. In some hospital or clinic environments, the doctor in charge of the treatment of a patient could be interested in programming the drop size and flow rate himself into the microprocessor of the monitoring device to take the responsibility for programming the medical device off the nurse's shoulders.

In this version of the monitoring device it can be connected to a PC 40 by inserting the USB plug 18 in the USB socket 17 (see FIG. 13), and the doctor can program the monitoring device's microprocessor and when the monitoring device is electrically connected to the medical device, the medical device's microprocessor, so that the medical device will work with a specific drop size and flow rate. Other functional parameters for the medical device can also be programmed by a doctor (or nurse) in this manner.

To make sure that a specific, individually programmed monitoring device is used for the treatment of the corresponding specific patient the doctor can write the patients name in the text field 10a (see FIGS. 14-15).

On the front of the monitoring device, the text "CUSTOMIZED" is applied to indicate that the monitoring device is specific and cannot be used for any but an intended medical device.

The medical device 1 can only be stopped and started with the monitoring device 9 inserted in the medical device and in electrical contact therewith. In hospitals and clinics where electronic journals are used it could be an advantage if the monitoring device is able to record and store data describing the treatment performed by the medical device. Then the doctor can connect the monitoring device via the USB connection to a PC and read the treatment data stored in the monitoring device and save them in the patients electronic journal.

Referring now to FIG. 16, in case the monitoring device 9 is programmed, for instance by a PC 40, it could be an advantage if a display 41 is provided in the housing 10 of the monitoring device. This display shows the data which the monitoring device has been programmed with. This will allow the medical device to perform more sophisticated treatments than just a fixed flow rate. For instance specify duration of the infusion, variation over time in flow rate, intermediated flow rates, Bolus option (for instance by pressing a specific key on the device) and bolus lock period.

The display can then show the specific features programmed, for instance as remaining time if a time limited treatment is programmed, bolus off/on if a bolus and a bolus lock period is programmed or a pause if an intermediate treatment has been programmed.

In FIG. 16, the display 41 displays the information "BOLUS-OFF" indicating that the bolus is in lock period.

In a further embodiment, the microprocessor incorporated in the PCB 33 of the medical device registers various data regarding the operation of the medical device and this data is communicated to the signal transmitter that transmits this data as a third signal to the monitoring device to be displayed by the display 41 such that the operation of the medical device can be monitored by a doctor or a nurse.

The invention claimed is:

1. A combination of a portable monitoring device for monitoring a medical device in the form of a portable drip infusion set for use in hospitals and the like and of the type comprising a liquid supply, a drip chamber downstream of said liquid supply for forming liquid drops and a flexible tube connecting said drip chamber with an injection needle, said monitoring device comprising:
a first housing, a signal receiver for receiving a first wireless signal, a first timing device for measuring a first time interval, an alarm device for emitting a first alarm, first electronic circuitry interconnecting said signal receiver, said first timing device and said alarm device for causing said alarm device to emit said first alarm if said first signal is not received by said signal receiver at the end of said first time interval, and a first battery for providing electric energy to said signal receiver, said alarm device and said timing device, and said medical device comprising:
a second housing, a signal emitter for emitting said first wireless signal, a second timing device for measuring said first time interval, second electronic circuitry interconnecting said timing device and said signal emitter for causing said signal emitter to emit said first signal at the end of said first time interval, and an electric power supply, preferably a second battery, for providing electric energy to said timing device and said signal emitter.

2. A combination according to claim 1, wherein said alarm device is adapted for emitting a second alarm and said signal emitter is adapted for emitting a second wireless signal, said monitoring device comprising third electronic circuitry adapted for registering receipt of said second signal by said signal receiver and causing said alarm device to emit said second alarm if said second signal is received by said signal receiver, and said medical device comprising fourth electronic circuitry being adapted for monitoring functional parameters of said medical device, any pre-determined output from said medical device or the function of said fourth electronic circuitry and further being adapted for registering deviations from pre-determined values of said functional parameters and causing said signal emitter to emit said second signal if said deviations are registered.

3. A combination according to claim 1, wherein said monitoring device and said medical device comprise first and second sets of electrical contacts, respectively, for mutually electrically interconnecting said monitoring device and said medical device for transmitting electronic data and/or electrical power between said monitoring device and said medical device.

4. A combination according to claim 3, wherein said medical device comprises programming means for programming fifth electronic circuitry controlling the function of said medical device, said fifth electronic circuitry comprising blocking means for blocking said programming function of said programming means when said monitoring device is not electrically connected to said medical device through said first and second electrical contacts.

5. A combination according to claim 3, wherein said monitoring device housing comprises an input port for receiving a data/electrical power plug, said input port being electrically connected to said first set of electrical contacts such that data and electrical power can be transmitted to said medical device from said input port when said first and second sets of electrical contacts are interconnected.

6. A combination according to claim 2, wherein said first and second alarms comprise one or more of a sensory alarm, a visual alarm and an audible alarm.

7. A combination according to claim 2, wherein said monitoring device housing comprises means for manually interrupting said first and second alarms.

8. A combination according to claim 3, wherein said first and second signals comprise a code recognizable by said first and third electronic circuitry of said monitoring device.

9. A combination according to claim 8, wherein said code is generated by fifth electronic circuitry of said medical device and transmitted to said first and third electronic circuitry of said monitoring device through said first and second sets of electric contacts.

10. A combination according to claim 5, wherein said electronic circuitry of the medical device comprises blocking means for blocking transmittal of data and electrical power to said medical device if said first and second electrical contacts are not in mutual electrical contact.

11. A combination according to claim 1, wherein said medical device and said monitoring device each comprise a microprocessor arranged in a printed circuit board (PCB), said microprocessors being in electrical contact for exchanging electronic data and said medical device microprocessor controlling the operation of said medical device.

12. A combination according to claim 11, wherein said monitoring device microprocessor is pre-programmed to transmit solely one specific set of operating instructions to said medical device microprocessor.

13. A combination according to claim 1, wherein said housing of said monitoring device is provided with a display adapted for displaying information in a visual manner.

14. A combination according to claim 11, wherein said display is adapted for displaying information generated by said monitoring device microprocessor.

15. A combination according to claim 11, wherein said signal emitter is adapted for emitting a third wireless signal comprising operational data of said medical device generated by said medical device microprocessor.

16. A combination according to claim 15, further comprising a display means adapted for displaying information based on said operational data transmitted by said third wireless signal and received by said signal receiver of said monitoring device.

17. A method of monitoring the function of a medical device for use in hospitals and the like in the form of a portable drip infusion set of the type comprising a liquid supply, a drip chamber downstream of said liquid supply for forming liquid drops and a flexible tube connecting said drip chamber with an injection needle, the method comprising the steps of:
- providing a portable monitoring device able to receive wireless signals from said medical device,
- causing said medical device to send a first wireless signal at certain time intervals, and
- causing said monitoring device to emit a first alarm if said monitoring device does not receive said first signal after said time interval has elapsed, wherein said medical device and said monitoring device each are provided with collaborating electrical contacts for establishing direct electrical contact between said monitoring device and said medical device for transmitting electrical energy and electronic data, and wherein the functions of said medical device are programmable only when said direct electrical contact is uninterrupted.

18. A method according to claim 17 and comprising the further steps of:
- causing said medical device to send a second wireless signal if said medical device develops a malfunction,
- causing said monitoring device to emit a second alarm if said monitoring device receives said second signal.

19. A method according to claim 17 and comprising the steps of:
- electrically connecting said monitoring device to said medical device,
- programming the functions of said medical device,
- removing said monitoring device from electrical contact with said medical device, and
- monitoring said monitoring device so as to register whether an alarm is emitted by said monitoring device.

20. A method according to claim 17 and comprising the steps of:
- causing said medical device to generate a code,
- transmitting said code to said monitoring device,
- incorporating said code in said first and second wireless signals.

21. A method according to claim 17, wherein said medical device comprises a first microprocessor for controlling the function of said medical device and said monitoring device comprises a second microprocessor adapted to communicate with said first microprocessor when said monitoring device is in electrical connection with said medical device.

22. A method according to claim 21 and comprising the steps of:
- programming said second microprocessor,
- electrically connecting said monitoring device with said medical device, and
- transmitting data from said second microprocessor to said first microprocessor.

23. A method according to claim 21 and comprising the steps of:
- generating operating data regarding the functioning of said medical device in said first microprocessor,
- transmitting said operating data to said monitoring device,
- storing said operating data in said monitoring device, and
- transmitting said operating data from said monitoring device to an electronic entity.

24. A method according to claim 17, wherein said monitoring device is provided with a display and comprising the further step of displaying information relative to the specific programming of said monitoring device by means of said display.

25. A method according to claim 23 and comprising the further step of causing said medical device to transmit said operating data to said monitoring device by means of a third wireless signal.

26. A method according to claim 23 and comprising the further step of displaying said operating data by means of a display.

* * * * *